United States Patent

Hollands

[11] Patent Number: 5,662,628
[45] Date of Patent: Sep. 2, 1997

[54] COUPLING

[75] Inventor: Keith G. M. Hollands, Sompting, England

[73] Assignee: E. R. Squibb & Sons, Inc., Princeton, N.J.

[21] Appl. No.: 631,459

[22] Filed: Apr. 12, 1996

[30] Foreign Application Priority Data

Apr. 13, 1995 [GB] United Kingdom ............. 9507667

[51] Int. Cl.$^6$ .................................................. A61F 5/44
[52] U.S. Cl. ........................ 604/342; 604/332; 285/317
[58] Field of Search ............................ 604/332, 338, 604/339, 342–344; 285/317, 321, 415, 921

[56] References Cited

FOREIGN PATENT DOCUMENTS 9101119  2/1991  WIPO ................................. 604/338

Primary Examiner—Robert A. Clarke
Attorney, Agent, or Firm—Stuart E. Krieger

[57] ABSTRACT

A coupling, which may be an ostomy coupling but could be any kind of tube or pipe coupling, includes a first coupling member 10 and a second coupling member 30 which are mutually interengageable and which surround an orifice 70. The coupling also includes a resilient split ring 50 which encircles the two coupling members and has a handle member 51 which can be manipulated to cause the split ring to be deformed. This causes the radially-inwardly extending tabs 52 on the ring to be shifted between respective first positions in which the split ring is undeformed and the tabs lock the two coupling members together and respective second positions in which the split ring is deformed in such a way as to shift the tabs radially outwardly to positions where they permit separation of the two coupling members.

The split ring is desirably made of a relatively rigid but springy plastics material, for example an acetal resin. The tabs carried by it are provided with curved or angled ramp surfaces which, when the ring is deformed by a force tending to rotate it relative to the coupling members, cause the tabs to be withdrawn from slots in one of the coupling members so permitting the two coupling members to be separated.

17 Claims, 5 Drawing Sheets

COUPLING

BACKGROUND OF THE INVENTION

This invention relates to a coupling.

One practical realisation of this invention is envisaged as residing in an ostomy coupling. The term "ostomy" is intended to include colostomy, ileostomy, urostomy and other surgical diversion procedures.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable world-wide commercial success is described and claimed in U.K. Patent No. 1,571,657.

An ostomy coupling in which locking and unlocking is achieved by deforming a ring is disclosed in our U.K. Patent Application No. 9409037.0, filed 6 May 1994.

An ostomy appliance in which a V-section ring holds coupling members together is disclosed in U.S. Pat. Nos. 5,322,522 and 5,322,523.

In PCT Application WO91/01119, published 1991 and corresponding to European Patent 482 104B, there is disclosed a locking ring for an ostomy coupling. An ostomy coupling which embodies such a ring is shown in European Patent 572 378B. Features of this design are that inwardly sprung tongues on the ring peripherally surround the joined coupling parts and that a press-button engagement device as well as a hook and detent engagement device are included, apparently in a quest for secure rotation of the locking ring on the coupling parts. It appears inevitable that quite intricate manipulation of this design of coupling is needed when applying or removing the bag.

It has been proposed by Kubo, in Japanese Utility Model No. 62-11610, published February 1985, that an ostomy device should have a double female ring structure which can interengage with a male ring. The male ring may be on the bag and the female ring on a skin-attachable adhesive pad, or vice-versa. The outer ring on the female ring is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts.

This arrangement, though perhaps operable in theory, has serious disadvantages in practice, for example (i) to connect or disconnect it is necessary to hold the coupling at four places, approximately spaced at 90° intervals around the periphery, (ii) pressing on two diametrically opposed regions will tend to bend the coupling out of its normal plane and the forces applied may easily cause the body side pad to be partially (or wholly) detached from the skin of the wearer, also the need to press in both ends of the diameter fully, and simultaneously, means that releasing the bag side coupling is subject to uncertainty, (iii) the repeated attachment and withdrawal of the bag side coupling part will cause the o-ring (provided to prevent escape of excreted matter between the male and female rings) to become worn, so compromising its sealing qualities with potentially highly embarrassing and undesirable results, (iv) the wearer may find it difficult to determine whether or not the two coupling parts are accurately arranged, (v) the accuracy and forces needed for manipulation to connect or disconnect will be well beyond the capability of an infirm, confused, elderly or impatient wearer; (vi) it is hard to be sure that the appliance is properly locked; and (vii) in the case of large sizes, the old and infirm will find it physically difficult to span with their hand and push in diametrally opposed regions of the ring. A further disadvantage of Kubo and of many present day ostomy couplings is that they extend outwardly from the body an undesirable distance, and so cause bulges or bumps under the wearer's clothing.

It is an aim of this invention to provide an improved design.

SUMMARY OF THE INVENTION

According to the present invention, there is provided a coupling including a first coupling member and a second coupling member which are mutually interengageable and which surround an orifice, the coupling also including a resilient split ring which encircles the two coupling members and has a handle member which can be manipulated to cause the split ring to be deformed such that radially-inwardly extending tabs on the ring are shifted between respective first positions in which the split ring is undeformed and the tabs lock the two coupling members together and respective second positions in which the split ring is deformed in such a way as to shift the tabs radially outwardly to positions where they permit separation of the two coupling parts.

According to a preferred embodiment of the invention, the split ring is made of a relatively rigid but springy plastics material, for example an acetal resin, and the tabs carried by it are provided with curved or angled ramp surfaces which, when the ring is deformed by a force tending to rotate it relative to the coupling members, cause the tabs to be withdrawn from slots so permitting the two coupling members to be separated.

In an advantageous embodiment of the invention, the split ring can be rotated relative to one of the coupling members, and rotary movement of the split ring is limited by virtue of a pair of arcuately-spaced studs on the first coupling member. These studs co-operate with a stud on the spill ring, and the split ring has its free ends shaped so that these ends are kept partly captive by a stop on the fast coupling member.

A valuable feature of the invention is that the split ring is reliably maintained on the first coupling member even when the second coupling member is removed therefrom. Additionally, when the first and second coupling members are coupled together, the handle on the ring is accessible at an upper region of the coupling, and cannot be shifted beyond its two limit positions. In one of these the coupling is locked and in the other, unlocked.

BRIEF DESCRIPTION OF THE DRAWINGS

The invention will be better understood from the following description of an illustrative example thereof, given with reference to the accompanying drawings in which.

DETAILED DESCRIPTION OF THE INVENTION

The present invention has been developed with a view to meeting the need for an ostomy coupling which can be easily manipulated by old or infirm and sometimes confused persons to separate a bag side coupling from a body side coupling member which is attached to a medical grade adhesive pad. As well as permitting easy manipulation, the invention aims to substantially avoid pressure on the tender peristomal area and to provide clear and unmistakable indications when the coupling members are (a) unlocked and ready for separation, and (b) locked together. This is a feature of importance to ostomates, who need to feel comfortable that no leakage will occur.

Figure 5:
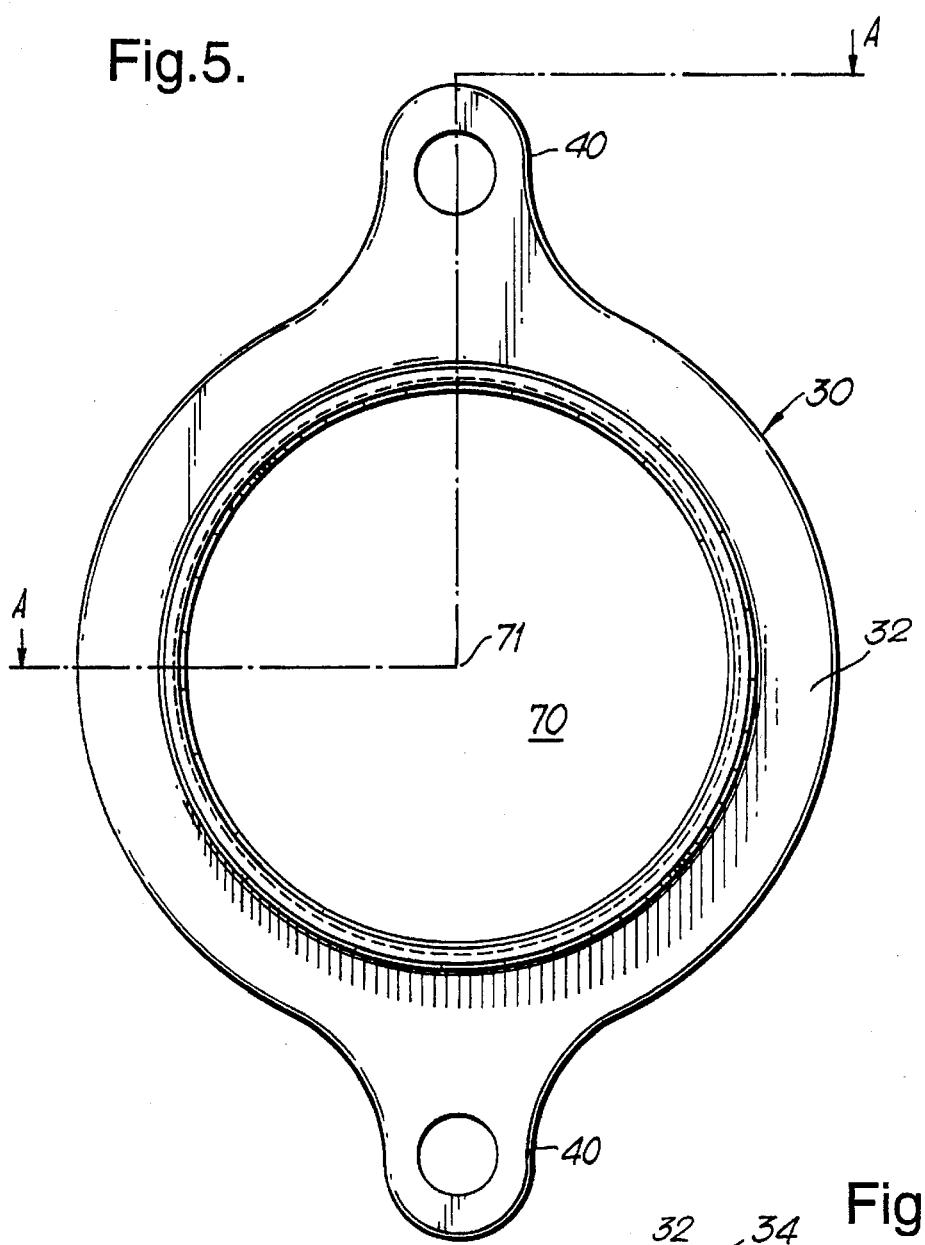
FIG. 5 is a plan view of a second coupling member pursuant to the present invention.
Figure 6A:
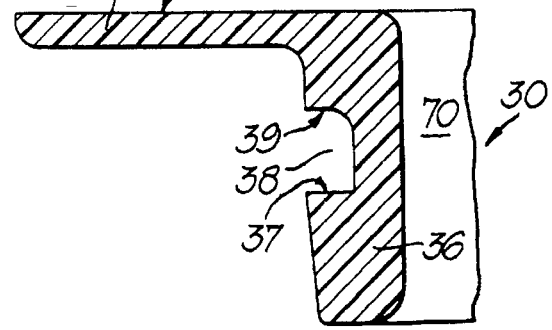
FIG. 6A is a partial cross section of the flange of the second coupling member of FIG. 5.
Figure 6:
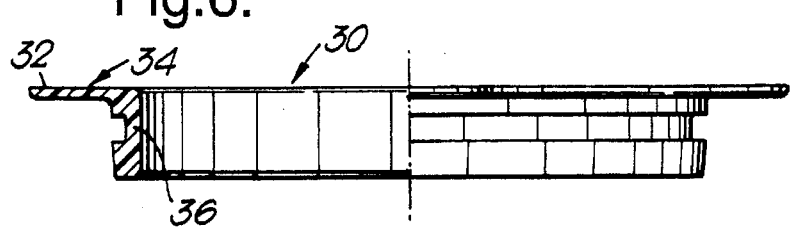
FIG. 6 is a side elevational view, in partial cross section, of the second coupling member of FIG. 5.
Figure 7:
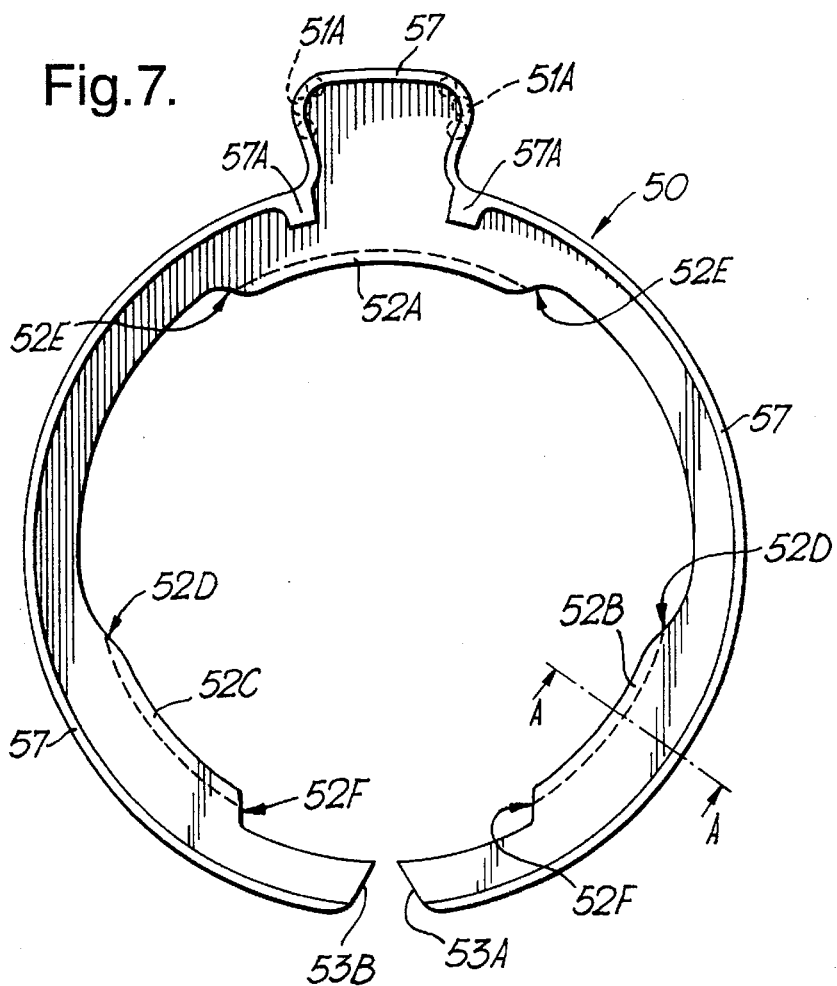
FIG. 7 is a rear view of one embodiment of split ring usable in a coupling according to the invention.
Figure 7C:
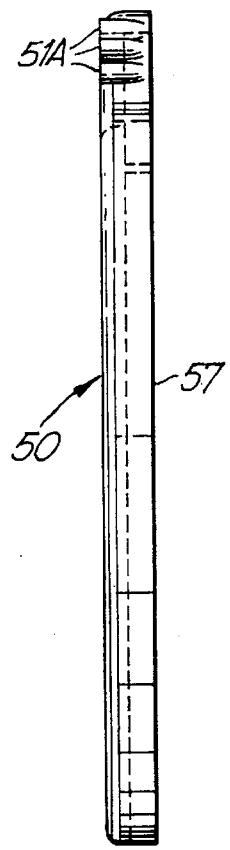
FIG. 7C is an edge view of the ring shown in FIG. 7.
Figure 7A:
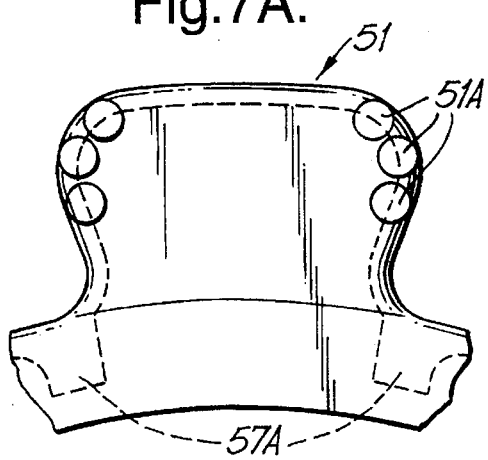
FIG. 7A is an enlarged view of the handle of the split ring, showing the front as compared to FIG. 7.
Figure 7B:
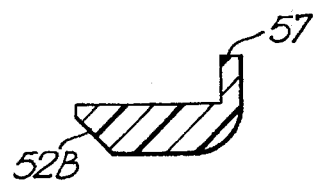
FIG. 7B is a cross-sectional view on the line A—A of FIG. 7 of a detail of the ring.

A preferred embodiment of a coupling according to the present invention comprises three parts, a first coupling member 10, FIGS. 1–4; a second coupling member 30, FIGS. 5 to 6A; and a locking ring 50, FIGS. 7 to 7C.

Figure 8:
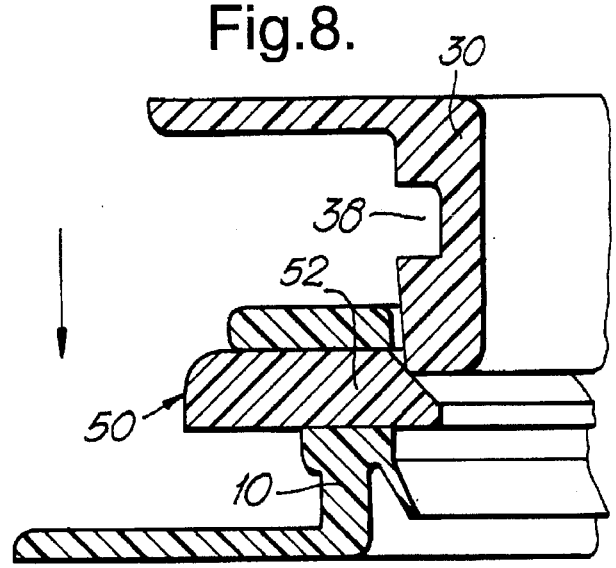
FIG. 8 is a cross-sectional view showing the initial stage of the coupling and locking of the first coupling, split locking ring and second coupling.
Figure 9:
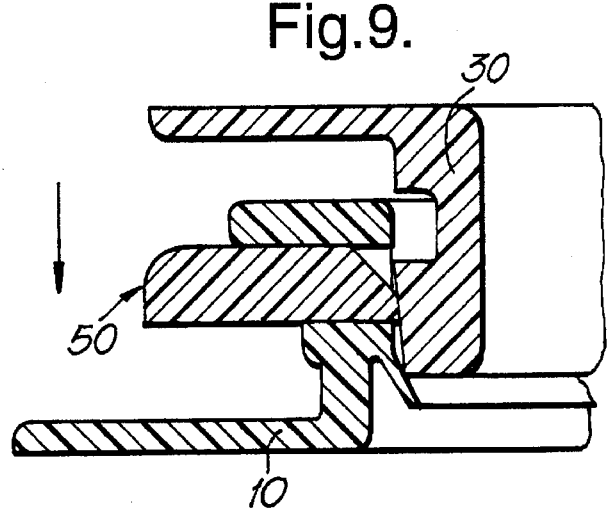
FIG. 9 is a cross-sectional view showing the intermediate stage of the coupling and locking of the first coupling, split locking ring and second coupling.
Figure 10:
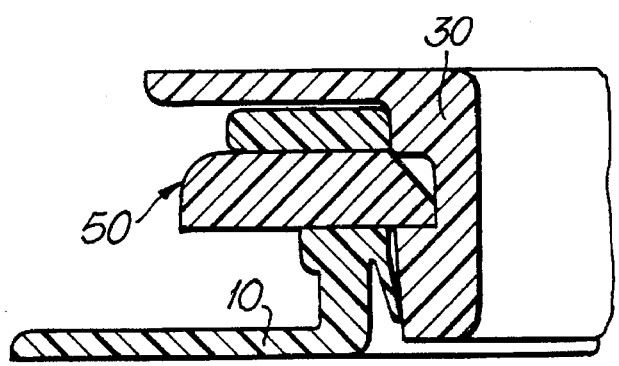
FIG. 10 is a cross-sectional view showing the final stage of the coupling and locking of the first coupling, split locking ring and second coupling.

Referring firstly to FIGS. 8–10, the bag side coupling member 30 in use is presented to and engaged with the body side coupling member 10 which is attached to the peristomal area in the normal way. The member 30 is pushed into the body side member 10 as shown by the arrow. FIG. 9 shows an intermediate stage in the coupling operation; the split ring 50 has been deformed so that a limb thereof is shifted radially outwardly as the part 30 slides past the chamfer on the tab 52 of the ring 50. FIG. 10 shows the completion of the action; ring 50 springs back into the recess 38 in the part 30 and holds the two coupling members locked together. Uncoupling is effected by a rotational movement of the split ring 50 achieved by pushing the handle portion of the ring to rotate the ring, as will be explained in more detail later in this specification.

Referring now to FIGS. 1–4, the first coupling member 10 will usually be the body side coupling member, and the second, the bag side member. However, without departing from the invention, the first coupling member could be the bag side member and the second coupling member could be the body side member, although this arrangement is currently less preferred.

The body side coupling member 10 may be an injection moulding made of high or low density polyethylene, and comprises a flange 12 having a surface 14 which in practice is attached in any suitable way such as by adhesive or by heat or RF or ultrasonic welding to a pad of medical grade adhesive. The purpose of such a medical grade adhesive pad is to attach the ostomy appliance to the skin of the wearer. The pad comprises a base which is preferably a thin film of polymeric material such as polyethylene and an adhesive layer situated on the rear surface of a base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents. Medical grade adhesive pads of other compositions may alternatively be used.

Figure 1:
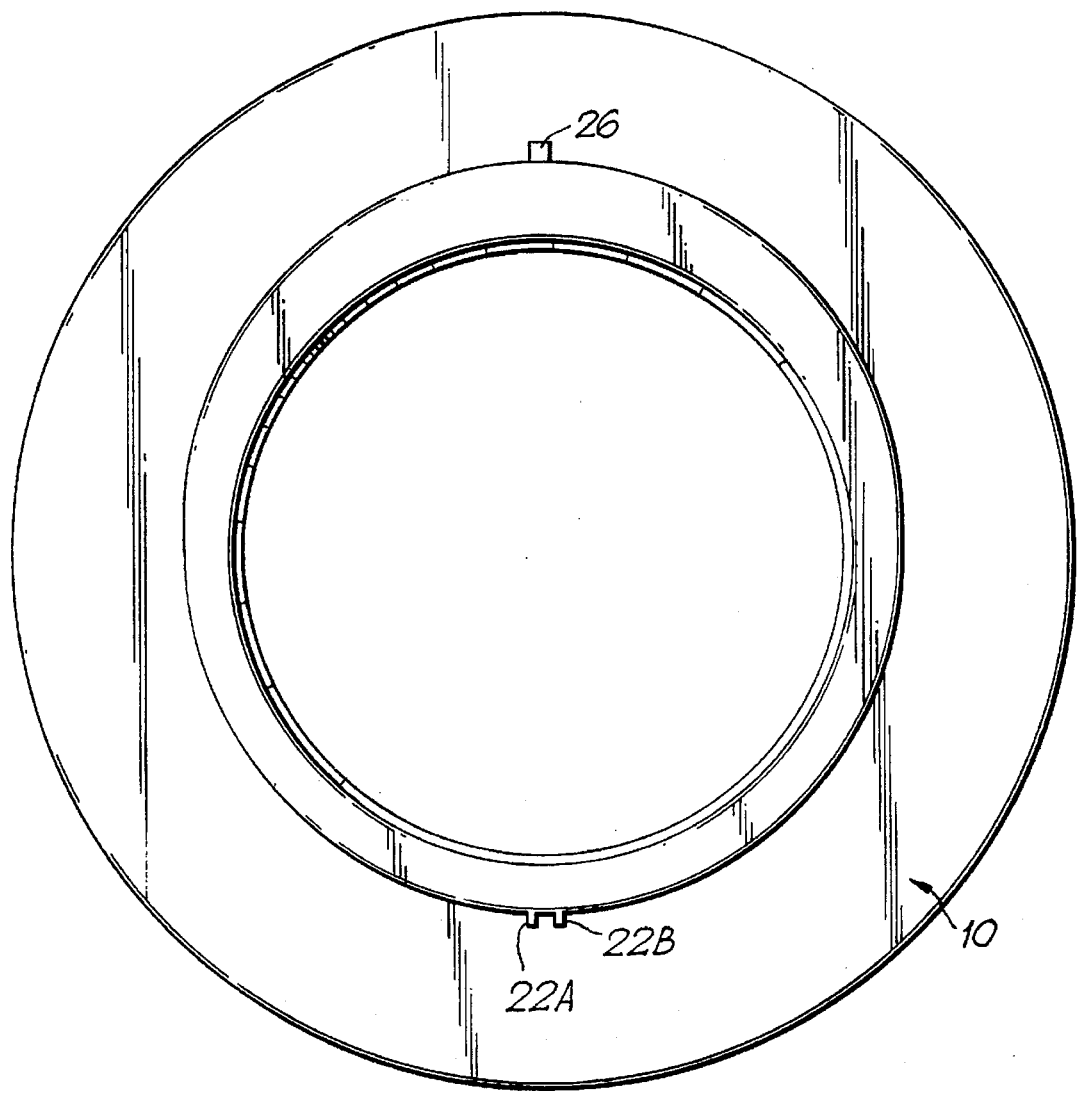
FIG. 1 is a plan view of a first coupling member pursuant to the present invention.
Figure 2:
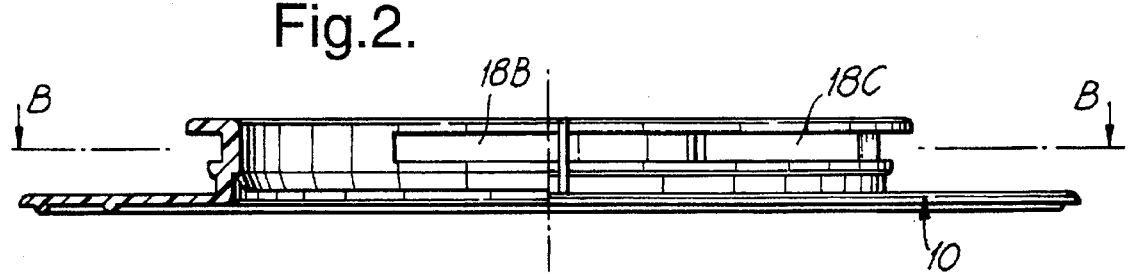
FIG. 2 is a side elevational view, in partial cross-section, of the first coupling member shown in FIG. 1.
Figure 3:
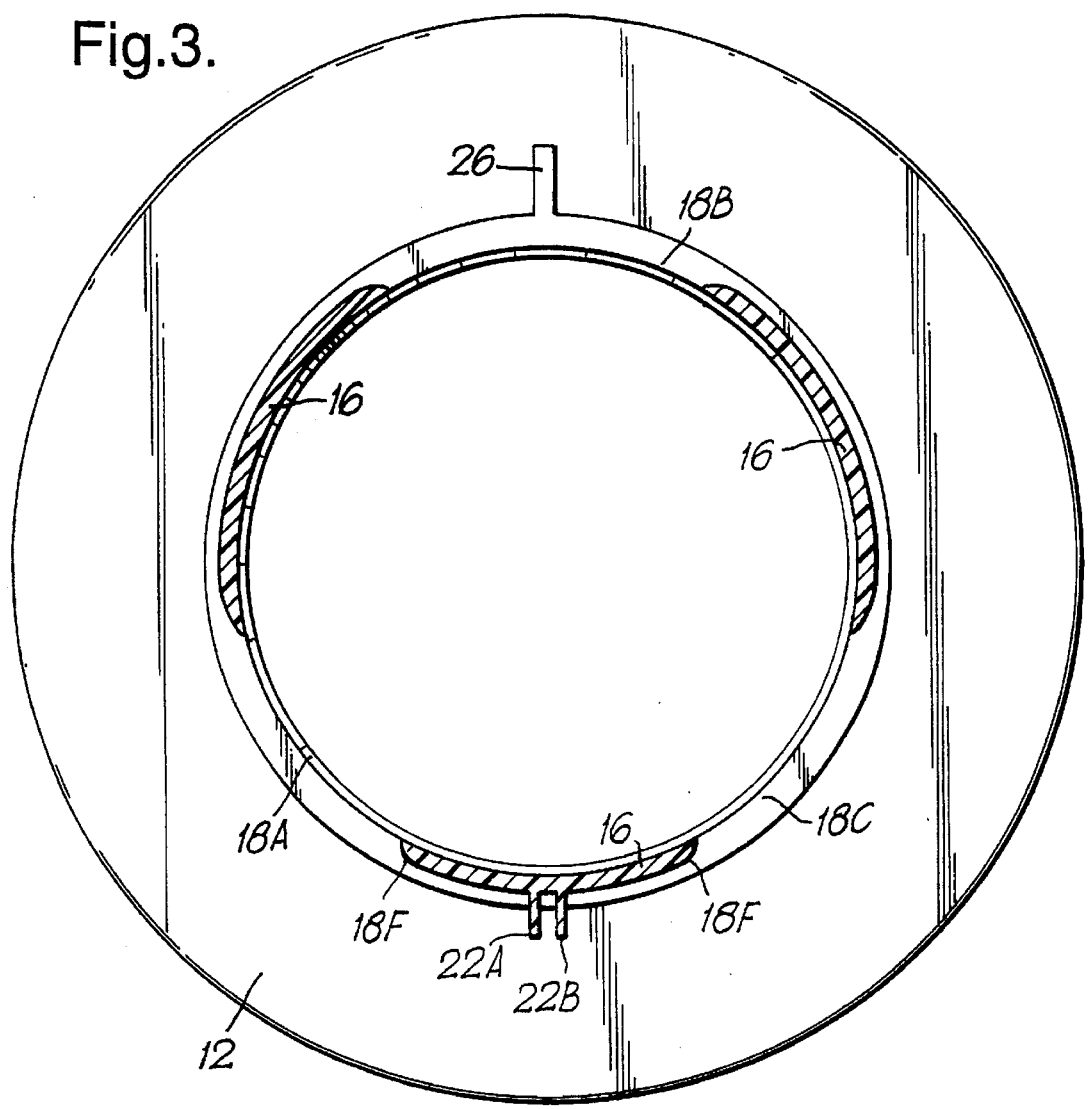
FIG. 3 is a cross-sectional view taken along line B—B of FIG. 2.
Figure 4:
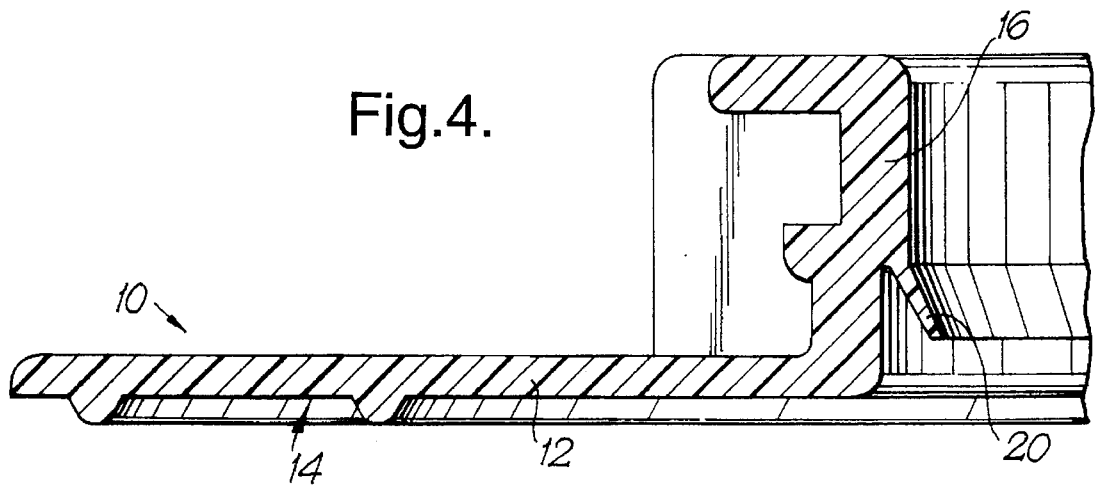
FIG. 4 is a side elevational view, in partial cross section, of one end of the first coupling member shown in FIG. 1.

The body side coupling member 10 also has a peripheral wall 16, which as seen in FIG. 2 is circular with three apertures 18A, 18B and 18C therein. The aperture 18A at the top of the coupling member (in normal position of wear) subtends about 65°, and each of the apertures 18B and 18C subtends about 50°. While in a preferred embodiment of the invention and as illustrated the first and second coupling members are generally circular in form, the invention is not considered to be limited to this, and the coupling members instead could be oval or other closed-loop shape. For brevity of description, however, circular coupling members are referred to. The wall 16 is upstanding from the flange 12, and, as seen best in FIG. 4, has a groove 28 in an external surface thereof, to receive tabs of the locking ring which will be later described. A further flange 17 extends radially outwardly from the wall 16.

At the base of the wall 16, extending inwardly, is a continuous, optionally resilient, deflectable sealing strip 20 (FIG. 4) which extends around the stoical orifice 70. The chief function of this strip is to inhibit leakage but it also serves to accommodate tolerances if during moulding of the coupling members, some slight divergence from the designed dimensions should occur.

At the opposite end of a diameter from the aperture 18B, on the external surface of the wall 16, there is provided a stop which is formed by a pair of nibs or walls 22A,22B, which project outwardly from the wall 16 and are also integral with the flange 14. Of course a single rib could be used instead. The end of the wall 16 remote from the flange 12 may optionally have an external chamfer. As seen in FIG. 10, in the assembled condition of the coupling members, the wall 16 of the body side member 10 surrounds the bag side member 30.

The radially external surface of the wall 16 has a groove 28 therein, extending completely around the wall 16. A lug 26, FIG. 2, extends radially outwardly externally of the wall 16, and serves to limit the extent of arcuate motion of a handle portion 51 of a split ring 50, FIG. 7, as will be later described.

The flange 17 of the body side coupling member 10 is shaped so that its maximum width is at a region which is at the top of the coupling in the normal position of wear. Its width decreases as one moves around the coupling to the 90° and 270° locations; its width is uniform over substantially the bottom half of the coupling. The purpose of this widening of the flange is to more securely retain the split ring 50.

Referring now to FIGS. 5, 6 and 6A, these depict a bag side coupling member 30 which is of simple design. The bag side coupling member 30 may also be an injection moulding and may be of EVA. It comprises a flange 32, having a surface 34 to which an ostomy bag or pouch (not shown) is attached. Extending from the flange, at right angles thereto (although other angles would be possible) is a cylindrical wall 36 which, as indicated above, in use fits within the wall 16 of the first coupling member. A groove 38 in the radially external surface of the wall 36 extends completely around that wall and has a flat surface 37 remote from the flange 32 and a curved surface 39 nearer to the flange 32, these surfaces 37 and 39 bounding the channel or groove 38. Belt attachment tabs 40 and a pull tab (not shown) may optionally be included. However, the inventor's present view is that such tabs can be dispensed with since, in the unlocked condition, the two coupling members can be quite readily separated by simply grasping the flange 32 between finger and thumb and pulling the second coupling member directly (axially) away from the first coupling member 10. As will be appreciated, the first and second coupling members surround a stomal orifice 70, into which normally projects the stoma of the person who has under R surgery.

Referring now to FIGS. 7, 7A, 7B and 7C, these depict a preferred embodiment of locking ring 50 for use in the present invention. This is a split ring of generally circular formation made of a relatively rigid but springy plastics material such as an acetal resin. For example, good results have been achieved with an acetal copolymer known as "KEMATAL" (Regd. Trade Mark) which is also referred to as polyoxymethylene (POM) and is available from Hoechst. This is a crystalline thermoplastic with an exceptionally stable polymer structure; a suitable grade is "HOSTAFORM" (Regd. Trade Mark) C.27021.

The ring 50 is a split ring and has free ends 53A and 53B. It is depicted in FIG. 7 in its normal or unstressed condition. The split ring 50 comprises a handle 51 and three inwardly projecting tabs, 52A, 52B and 52C. The tabs 52B and 52C are located around the ring at about 135 degrees from top dead centre (i.e. the centre of the handle 51). The tabs project inwardly from an inner surface of the ring 50 and are integral with it. The extent of inward projection is determined according to the radius of the ring. As will be appreciated, ostomy couplings are made in various sizes, ranging from about 32 millimeters to about 57 millimeters. The larger sizes would be used post-operatively, and would have tabs which are wider in the radial direction. More than three tabs could be included, if desired.

The tab 52A is provided with smoothly-sloping end portions 52E. The tabs 52B and 52C have relatively shallowly-sloped surfaces 52D at their respective ends nearer to the handle 51, and at their ends further from the handle 51 they have sloped surfaces 52F at about 25° or 30° to the diametral direction. The smooth shallow slope of the surfaces 52D assists in enabling the handle (and hence the ring 50) to be freely movable within limits in a rotational direction. As shown, the surfaces 52E are radiused, a suitable radius being about 3 millimeters. The shape of these tabs 52B and 52C is of importance to the satisfactory operation of the coupling.

The split ring 50 has a wall 57. The wall 57 extends around the split ring as seen in FIG. 7 and merges with two stop blocks 57A which limit the possible rotation of the ring: that is, one or other of the blocks 57A engages the radial (top dead centre) rib 26 on the body side coupling member 10, so limiting the rotation of the ring relative to the body side coupling member. This wall also serves as a spacer which ensures that the tabs 52A, 52B, 52C are correctly positioned to enter into recesses ISA, B, C. The handle 51 optionally has circular pips 51A thereon (see FIGS. 7 and 7A) to provide a rough surface which can be gripped. This makes shifting the ring an easier task for elderly or infirm users. To avoid the handle 51 catching in clothing, it is preferably canted inwards, towards the body side coupling member, by a few degrees. The free ends of the split ring have angled surfaces 53A and 53B. In use these surfaces co-operate with the nibs 22A and 22B of coupling member 10. That is to say, when the ring 50 is rotated as described, either the surface 53A or the surface 53B, depending upon the direction of rotation, comes into engagement with, and is held in engagement with, the nib 22A or 22B as the case may be.

When it is desired to unlock the coupling and thereby release the bag side member so that it may be axially drawn off the body side coupling member, the handle 51 is rotated a short distance, e.g. about 5° to 10°, in either rotary direction away from its central position. The extent of this movement is limited by engagement of one of the stops 57A with the stop lug 26.

As a result, the tab 52B, FIG. 7, is shifted circumferentially in a clockwise direction, and its surface, e.g. 52D rides up on the edge of the corresponding aperture. Thus, the tabs are forced in directions approximately radially outwardly, this being permitted by the springy nature of the material of the ring 50. In other words, the free end of the split ring in effect pivots substantially about the point of engagement of its tip 53C with the junction of the wall 16 and base of the nib (22A or 22B as the case may be).

As will be understood, although not illustrated, as a consequence of rotation of the handle, the other tab 52C will similarly be forced generally radially outwardly and the tab 52A will also be forced radially outwardly, resulting in the formerly inwardly projecting locking portions of the tabs 52A, B, and C being withdrawn so they no longer extend into the channel 38 of the coupling 30. The springy nature of the limbs of the ring enables the handle region 51 of the ring 50 to move a short distance radially away from the central longitudinal axis 71 (FIG. 5) of the stomal orifice 70. Also this rotary movement of the ring 50 causes the surface 53A or 53B of a free end of the ring to come into engagement with the nib 22A or 22B. Due to the relative shapes of these parts, that end 53A or 53B of the ring 50 remains wedged against the nib. With the parts in these positions, it is readily seen that the tabs 52 are withdrawn from the stomal orifice 70 and the bag and bag side coupling member thereon can be removed by a gentle axial pull.

Tests have shown that an ostomy coupling as described above satisfactorily meets exacting requirements for performance, as set out below.

TABLE I

| Test | Result |
| --- | --- |
| Average gas loss through coupling (at 0.25 to 0.35 psi) | 0.016 ml. per minute |
| Average pull-off force at tab | 71.4 N. |
| Average pull-off force between tabs | 62.6 N. |
| Average force to couple the bag and body side members | 9.4 N. |

It will be seen that the particular embodiment of the invention described herein provides a coupling which can be easily disassembled and assembled by persons who are not nimble, which can be assembled and disassembled with only very light pressure being applied either during coupling or uncoupling to the tender peristomal area, and which can readily be made in any coupling size. The ring 50 is in effect made captive within the coupling members 10 and 30, and so cannot escape; moreover, the positive rotational movement of the handle 51 between two fixed positions gives assurance to the wearer such that he or she knows when the coupling is properly locked, because in the properly locked condition, the handle is at top dead centre. In a further embodiment of the invention, by choosing an appropriate springiness of the material for the locking ring 50, the ring can be made to automatically spring back towards top dead centre position when the wearer releases his/her grip of the handle 51. While a ring having three tabs is currently preferred, four or more could be employed.

What is claimed is:

1. A coupling comprising:
    a first coupling member and a second coupling member which are mutually interengageable and which surround an orifice, at left one of said coupling members having tab receiving slots; and
    a resilient split ring encircling said two coupling members having radially inward extending lockable tabs, said split ring being manipulatable to cause said split ring to be deformed so that said radially-inwardly extending tabs on said ring are shifted between first positions in which said split ring is undeformed and said tabs are received in said slots and said two coupling members together and respective second positions in which said lock split ring is deformed so as to shift said tabs radially outwardly to locations where they permit separation of said two coupling members by retracting said tabs from said slots.

2. The coupling according to claim 1 wherein said split ring is made of a relatively rigid and springy plastic material, and said tabs include angled ramp surfaces which, when said ring is deformed by a force tending to rotate it relative to said coupling members, cause said tabs to be withdrawn from said slots permitting said two coupling members to be separated.

3. The coupling according to claim 1 wherein said split ring is rotatable relative to one of said coupling members, and said rotary movement of said split ring is limited by a pair of arcuately-spaced studs on said first coupling member, said studs cooperating with a stop on said split ring.

4. The coupling according to claim 1 wherein one said two couplings is adapted to be secured to an ostomy pouch and the other of said couplings is adapted to be secured to a member attachable to a body.

5. The coupling according to claim 4 wherein said tabs on said split ring have surfaces which are sloped for enabling said tabs to be forced substantially radially outwardly by the insertion of said second coupling member into said first coupling member.

6. The coupling according to claim 5 in which said free ends of said split ring have substantially flat surfaces which are located at approximately 250° to 350° to a line bisecting said ring and passing between said free ends.

7. The coupling according to claim 6 wherein three tabs are spaced around said split ring and said second coupling member has three apertures complementary to said tabs.

8. The coupling according to claim 1 wherein said split ring is rotatable relative to one of said coupling members, and said rotary movement of said split ring is limited by a pair of arcuately spaced studs on said split ring, said studs cooperating with a stop on said first coupling member.

9. The coupling according to claim 1 wherein said split ring has free ends and said first coupling member has a stop, said step limiting the rotational movement of said split ring.

10. An ostomy coupling including a first coupling member and a second coupling member which are mutually interengageable and which surround a stomal orifice, at lease one of said coupling members having tab-receiving slots; said coupling also including a resilient deformable split ring which is made of a relatively rigid and springy plastic material, said split ring having inwardly extending tabs thereon, said tabs being provided with ramp surfaces which, when said ring is deformed by a force tending to rotate it relative to said coupling members, cause said tabs to slide on end surfaces of the respective slots so that they are withdrawn from slots in one of said coupling members, permitting said two coupling members to be separated.

11. The ostomy coupling according to claim 10 wherein said split ring is made of an acetal resin.

12. An ostomy coupling comprising:
    a first coupling member and a second coupling which are mutually interengageable and which surround an opening for receiving a stoma, one of said couplings being adapted to attach to skin, the other of said coupling being adapted to attach to a pouch,
    a resilient split ring encircling said two coupling members having radially inward extending lockable tabs, said split ring being manipulatable to cause said split ring to be deformed so that said radially inwardly extending tabs on said split ring are shifted between first positions in which said split ring is undeformed and said tabs are received in said slots and lock said two coupling members together and respective second positions in which said split ring is deformed so as to shift said tabs radially outwardly to locations where they permit separation of said two coupling members by retracting said tabs from said slots.

13. The ostomy coupling of claim 12, wherein said split ring includes a projection facilitating manual manipulation of said split ring.

14. The ostomy coupling of claim 12, wherein said split ring is rotatable when manipulated and said split ring is deformed when it is rotated.

15. The ostomy coupling of claim 14, wherein said tabs have sloped surfaces facilitating their retraction from said slots when said split ring is rotated.

16. The ostomy coupling of claim 15 wherein said locking ring is rotatable and said locking ring is deformed when it is rotated.

17. An ostomy coupling comprising:
    first and second coupling members capable of being coupled together, each of said members having a central stomal opening, said first coupling member having a flange with a projection receiving channel, said channel being defined at least in part by a concentric inner and outer wall, said inner wall being positioned closer to said stomal opening, said outer wall having a plurality of tab-receiving slot's therein, said second coupling member having a projection receivable in said channel when said first and second members are coupled together, said projections being lockable in said channel, and
    a resilient deformable releasably lockable locking ring positionable circumferentially about said outer wall, said locking ring including a plurality of tabs projecting radially inwardly into said slot so as to lock said projection in said channel when said coupling members are coupled together, said tabs being withdrawable from said slots so as to unlock said projection when said locking ring is deformed.

* * * * *